United States Patent [19]

Spivack et al.

[11] Patent Number: 4,692,532
[45] Date of Patent: Sep. 8, 1987

[54] SUBSTITUTED N-(4-HYDROXYPHENYLTHIOALKYL) CYCLIC IMIDES

[75] Inventors: John D. Spivack, Spring Valley; Ramanathan Ravichandran; Stephen D. Pastor, both of Yonkers, all of N.Y.

[73] Assignee: Ciba-Geigy Corporation, Ardsley, N.Y.

[21] Appl. No.: 674,217

[22] Filed: Nov. 23, 1984

[51] Int. Cl.$^4$ .................. C07D 233/70; C07D 233/72; C07D 233/80; C07D 487/04

[52] U.S. Cl. ..................................... 548/312; 546/121; 548/302; 548/311; 548/319; 548/320; 548/512; 548/513; 548/544; 548/547; 548/551

[58] Field of Search ................ 546/121; 548/302, 311, 548/312, 319, 320, 478, 512, 513, 547, 551, 544

[56] References Cited

U.S. PATENT DOCUMENTS 3,562,292  2/1971  Grewe et al. ............... 548/478
3,956,313  5/1976  Freyermuth et al. ......... 548/551
4,124,375 11/1978  Bollinger et al. ........... 71/96
4,456,716  6/1984  Spivack et al. ............. 548/547
4,534,874  8/1985  Steinberg et al. ........... 548/320

OTHER PUBLICATIONS

Chem. Abst., 83, 131339d, (1975).
Chem. Abst., 84, 89841d, (1976).
*Hackh's Chemical Dictionary*, 4th Edit., 1969, p. 27.

Primary Examiner—Henry R. Jiles
Assistant Examiner—Kurt G. Briscoe
Attorney, Agent, or Firm—Harry Falber

[57] ABSTRACT

Substituted (4-hydroxyphenylthioalkyl) derivatives of the formula

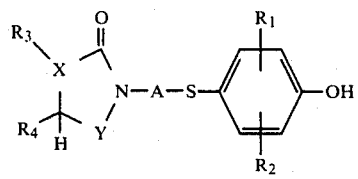

are prepared by the reaction of the appropriate ring and hydroxybenzene thiol compounds and are useful stabilizers of organic materials.

11 Claims, No Drawings

SUBSTITUTED N-(4-HYDROXYPHENYLTHIOALKYL) CYCLIC IMIDES

Organic polymeric materials such as plastics and resins, are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the (hydroxphenylthio alkyl) derivatives of this invention exhibit a variety of desirable properties which makes them particularly effective and useful as stabilizers. The compounds show excellent activity in protecting high impact polystyrene, rubbers such as polybutadiene and styrene-butadiene rubber, and other elastomers wherein retention of elasticity and inhibition of crosslinking, crazing, discoloration, odor formation and exudation are basic requirements.

Various phenylthio imide compounds have been disclosed in the prior art. U.S. Pat. No. 4,124,375 discloses substituted phthalimides which are structurally distinct from the instant compounds in the nature of the linking group and the absence of the hindered phenol group. These compounds are noted for regulating the growth of plants. U.S. Pat. No. 4,456,716 disclosed (hydroxyphenylthio)imide stabilizers which are structurally distinct in the nature of the linking group and in the substitution pattern. Chemical Abstracts 83, 131339d (1975) and Chemical Abstracts 84, 89841d (1976) disclose comparable cyclic imide antioxidants absent the sulfur atom in the bridging member.

It is the primary object of this invention to provide a class of imide, hydantoin and imidazolidone derivatives which exhibits a broad range of improved stabilization performance characteristics.

Various other objects and advantages of this invention will become evident from the following description thereof.

The compounds of this invention correspond to the formula

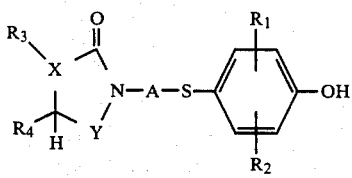

wherein $R_1$ and $R_2$ independently are hydrogen, alkyl of 1 to 18 carbon atoms, cycloalkyl of 5 to 6 carbon atoms, phenyl or phenyl substituted by alkyl of 1 to 12 carbon atoms;

$R_3$ and $R_4$ independently are hydrogen, alkyl of 1 to 18 carbon atoms, cycloalkyl of 5 to 6 carbon atoms, phenyl, phenyl substituted by alkyl of 1 to 12 carbon atoms or the group

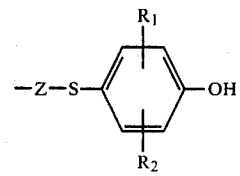

or together can also form a cycloalkyl, aryl or heterocyclic ring structure having from 5 to 7 members in the ring;

A is alkylene of 1 to 18 carbon atoms or subsituted alkylene of the formula $(R_5)(R_6)C<$ wherein $R_5$ and $R_6$ are independently hydrogen, alkyl of 1 to 12 carbon atoms or aryl;

X is, CH or nitrogen;

Y is $-CH_2-$ or

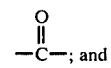

Z is A or a direct bond.

Preferred compounds within the above structure are those wherein $R_1$ is in the ortho position to the hydroxyl group in the phenyl ring.

The $R_1$ and $R_2$ groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the $R_2$ group to be in the ortho position to the hydroxy group, particularly if $R_2$ is tert-alkyl. Benzyl, α-methylbenzyl and α,α-dimethylbenzyl are also preferred.

The substituents on the phenyl in $R_1$ and $R_2$ are alkyl of 1 to 12 carbon atoms, and preferably 1 to 8 carbon atoms.

$R_3$ and $R_4$ are preferably hydrogen, alkyl of 8 to 18 carbon atoms or the hydroxyphenylthio group. The preferred ring structures include $C_5-C_6$ cycloalkyl, pyrrolidine, piperdine and phenyl.

A is preferably lower alkylene of the formula

wherein $R_5$ and $R_6$ are independently hydrogen, alkyl of 1 to 12 carbon atoms or aryl. Typical aryl groups include phenyl, tolyl, mesityl, xylyl and 1- and 2-naphthyl. Z is preferably the direct bond or the same aforementioned lower alkylene group.

The derivatives of this invention can be prepared by reacting the appropriately substituted imide, hydantoin or imidazolidone with an alkylated hydroxybenzene thiol optionally in a solvent, to yield the desired product. The solvent can be an aromatic hydrocarbon such a benzene, toluene, xylene, and the like, or a heterocyclic ether, such as tetrahydrofuran. The reaction temperature ranges from 0° to 70° C. The preferred method for preparing the compounds of this invention involves reacting the imide, hydantoin or imidazolidone with the thiol in the presence of a proton acceptor such as a tertiary amine including triethylamine or pyridine, or an alkali hydroxide. The starting materials needed to prepare the stabilizers of this invention are items of commerce or can be prepared by known methods. For example, preparative methods for preparing cyclic imides are described in Hargreaves, Pritchard and Dave, Chemical Reviews, 70, 439–469 (1970).

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/-butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylo nitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in various weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants
1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-isobutylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol
1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol
1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)
1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane)
2,6-di-(3-tert.butyl-5-methyl-2-hydroxybenzyl)-4-methylphenol
1,1,3-tris-(5-tert.butyl-4-hydroxy-2-methylphenyl)-butane   1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)butyrate], di-(3-tert.butyl-4-hydroxy-5-methylphenyl)-dicyclopetadiene
di-[2-(3'-tert.butyl-2'-hydroxy-5'-methylbenzyl)-6-tert.butyl-4-methylphenyl]-terephthalate.
1.5. Benzyl compounds, for example,
1,3,5-tri-(3,5-di-tert.butyl-4-hydroxybenzyl)-2,4,6-trimethylbenzene-di-(3,5-di-tert.butyl- 4-hydroxybenzyl)-sulfide
3,5-di-tert.butyl-4-hydroxybenzyl-mercapto-acetic acid isooctyl
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt
1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate
1.7. Esters of β-(3,5-di-tert.butyl-4-hydroxyphenyl)-propionic acid with monohydric or polyhydric alcohols, for example,

| methanol | diethyleneglycol |
|---|---|
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Esters of β-(5-tert.butyl-4-hydroxy-3-methylphenyl)propionic acid with monohydric or polyhydric alcohols, for example,

| methanol | diethyleneglycol |
|---|---|
| octadecanol | triethyleneglycol |
| 1,6-hexanediol | pentaerythritol |

| | |
|---|---|
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-,5'-(1,1,3,3-tetramethylbutyl)-, 5-chloro-3',5'-di-tert.butyl-,5-chloro-3'-tert.butyl-5'-methyl-, 3'-sec.butyl-5'-tert.butyl-,4'-octoxy, 3',5'-di-tert.amyl-, 3',5'-bis- (α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2', 4'-trihydroxy- and 2'-hydroxy-4,4'-dimethoxy derivative.

2.3. Esters of optionally substituted benzoic acids, for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert.butyl-oxanilide, 2,2'-didodecyloxy-5,5'-di-tert.butyl-oxanilide, 2-ethoxy-2'-ethyloxanilide, N,N'-bis (3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bisbenzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearylsorbite triphosphite, tetrakis-(2,4-di-tert.butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

N-(3,5-di-tert-butyl-4-hydroxyphenylthiomethyl)phthalimide

A vessel was charged with 12.19 grams of 3,5-di-tert-butyl-4-hydroxybenzene thiol and 3.30 grams of potassium hydroxide dissolved in 50 ml of acetone and 2 ml of water at 0° C. which was mixed with 10.0 grams of N-(chloromethyl)phthalimide. After stirring for one hour, the precipitated product was removed by filtration and then recrystallized from ethyl acetate-hexane to give 14.9 grams of produt, m.p. 151°–53° C.

Anal. Calc'd for $C_{23}H_{27}NO_3S$: C, 69.5; H, 6.9; N, 3.5. Found: C, 69.5, H, 7.0, N, 3.6.

EXAMPLE 2

N-(3-methyl-4-hydroxy-5-tert-butylphenylthiomethyl)phthalimide

The procedure of Example 1 was repeated using 8.46 grams of 3-methyl-4-hydroxy-5-tert-butylbenzenethiol, 1.72 grams of potassium hydroxide, and 8.43 grams of N-(chloromethyl) phthalimide . Recrystallization from ethyl acetate-heptane afforded 7.1 grams of product with m.p. 114°–116° C.

Anal. Calc'd for $C_{20}H_{21}NO_3S$: C, 67.6; H, 6.0; N, 3.9. Found: C, 67.7, H, 5.9, N, 3.9.

EXAMPLE 3

N-(3,5-di-tert-butyl-4-hydroxyphenylthiomethyl)-2-dodecen-2-yl-succinimide

A vessel was charged with 10.0 grams of N-(hydroxymethyl)2-dodecen-2-yl succinimide dissolved in 30 ml of methylene chloride at 0°–5° C., 7.1 ml of triethylamine followed by 2.9 ml of methanesulfonylchloride. After stirring for one hour, removal of solvent afforded the crude mesylate which was dissolved in 50 ml of acetone and treated with a solution of 8.05 grams of 3,5-di-tert-butyl-4-hydroxybenzenethiol and 1.35 grams of sodium hydroxide in 50 ml of acetone and 10 ml of water. After stirring for eight hours, the mixture was concentrated and the residue was partitioned between methylene chloride and water. The combined organic extracts were washed with water, brine dried ($MgSO_4$) and evaporated to give the crude product. Flash column chromatography (silica gel, 3:1, heptane:ethyl acetate) afforded 9.5 grams of pure product, m.p. 53°–55° C.

Anal. Calc'd for $C_{31}H_{49}NO_3S$: C, 72.2; H, 9.6; N, 2.7. Found: C, 72.0, H, 9.1, N, 2.6.

EXAMPLE 4

3-(3,5-di-tert-butyl-4-hydroxyphenylthiomethyl)-5,5-dimethyl hydantoin

The procedure of Example 3 was repeated using 10.0 grams of N-(hydroxymethyl)-3,3-dimethyl hydantoin, 5.38 ml of methanesulfonylchloride, 13.22 ml of triethylamine, 15.07 grams of 3,5-di-tert-butyl-4-hydroxybenzene thiol and 2.53 grams of sodium hydroxide. The crude product was recrystallized from ethyl acetate-hexane to give 15.2 grams of white solid, m.p. 160°–162° C.

Anal. Calc'd for $C_{20}H_{30}N_2O_3S$: C, 63.5; H, 8.0; N, 7.4. Found: C, 63.8, H, 8.0, N, 7.4.

EXAMPLE 5

N-(3,5-di-tert-butyl-4-hydroxyphenylthiomethyl)-2-(3,5-ditert-butyl-4-hydroxyphenylthio)succinimide The procedure of Example 3 was repeated using 10.0 grams of N-(hydroxymethyl)-2-(3,5-di-tert-butyl-4-hydroxyphenylthio)succinimide, 2.33 ml of methanesulfonylchloride, 5.72 ml of triethylamine, 6.52 grams of 3,5-di-tert-butyl-4-hydroxybenzene thiol and 1.09 grams of sodium hydroxide. Flash column chromatography ($SiO_2$, 5:1 heptane:ethylacetate) afforded 7.09 grams of product as white solid, m.p. 138°–140° C.

Anal. Calc'd for $C_{33}H_{47}NO_4S_2$:C, 67.7; H, 8.1; N, 2.4. Found: C, 67.7, H, 7.9, N. 2.2.

EXAMPLE 6

1,3-bis(3,5-di-tert.-butyl-4-hydroxyphenylthiomethyl)-2-imidazolidone

A solution of 3.65 grams of 1,3-bis(hydroxymethyl)-2-imidazolidone and 11.92 grams of 3,5-di-t-butyl-4-hydroxybenzenethiol in 100 ml of methyl alcohol was treated with anhydrous hydrogen chloride. The reaction mixture was cooled and the product recrystallized from methyl alcohol to give 11.43 grams of white solid, m.p. 173°–176° C.

Anal. Cald'd for $C_{33}H_{50}N_2O_3S_2$: C, 67.5; H, 8.6; N, 4.8. Found: C, 67.3, H, 8.7, N, 4.8.

EXAMPLE 7

Unstabilized polypropylene powder (Hercules Profax 6501) was thoroughly blended with the indicated amount of additive. The blended materials were then milled on a two roll mill at 182° C. for 5 minutes, after which time the stabilized polypropylene was sheeted from the mill and allowed to cool. The milled polypropylene was then cut into pieces and compression molded on a hydraulic press at 220° C. and 175 psi ($1.2 \times 10^6$ Pa) into 25 mil thick plaques. The sample was exposed in a fluorescent sunlight/black light chamber until failure. Failure is taken as the hours required to reach 0.5 carbonyl absorbance by infrared spectroscopy on the exposed films.

| Additive Compound of | Additive Conc. (% by weight) | FS/BL Test Results (Hours to Failure) |
|---|---|---|
| None | — | 100 |
| Example 1 | 0.2 | 190 |
| Example 2 | 0.2 | 220 |
| Example 3 | 0.2 | 220 |
| Example 4 | 0.2 | 250 |
| Example 5 | 0.2 | 290 |

These data thus indicate the effective stabilization activity of the instant compounds.

Summarizing, it is seen that this invention provides novel compounds which exhibit effective stabilization activity. Variations may be made in proportions, procedures and materials without departing from the scope of the invention as defined by the following claims.

What is claimed is:

1. A compound of the formula

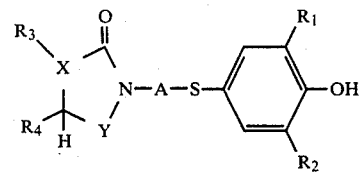

wherein
R$_1$ and R$_2$ independently are alkyl of 1 to 18 carbon atoms, cycloalkyl of 5 to 6 carbon atoms, phenyl or phenyl substituted by alkyl of 1 to 12 carbon atoms,
R$_3$ and R$_4$ independently are hydrogen, alkyl of 1 to 18 carbon atoms, cycloalkyl of 5 to 6 carbon atoms, phenyl, phenyl substituted by alkyl of 1 to 12 carbon atoms or the group

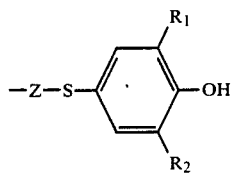

or together can also form cycloalkyl of 5 to 6 carbon atoms, pyrrolidine or piperidine;

A is alkylene of 1 to 18 carbon atoms or substituted alkylene of the formula $(R_5)(R_6)C<$ wherein $R_5$ and $R_6$ independently are hydrogen, alkyl of 1 to 12 carbon atoms or phenyl;

X is

or nitrogen;

Y is —CH$_2$—or

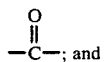; and

Z is A or a direct bond.

2. The compound of claim 1, wherein $R_1$ is alkyl of from 4 to 8 carbon atoms.

3. The compound of claim 2, wherein $R_1$ is tert.-butyl, tert.-pentyl or tert.-octyl.

4. The compound of claim 1, wherein $R_2$ is tert.-alkyl of from 4 to 8 carbon atoms.

5. The compound of claim 1, wherein A is substituted alkylene of the formula

wherein $R_5$ and $R_6$ independently are hydrogen, alkyl of 1 to 12 carbon atoms or phenyl.

6. The compound of claim 1, wherein X is CH.

7. The compound of claim 1, wherein X is nitrogen.

8. The compound of claim 1, wherein Y is

.

9. N-(3,5-di-tert-butyl-4-hydroxyphenylthiomethyl)-2-dodecen-2-yl-succinimide.

10. 3-(3,5-di-tert-butyl-4-hydroxyphenylthiomethyl)-5,5dimethyl hydantoin.

11. N-(3,5-di-tert-butyl-4-hydroxyphenylthiomethyl)-2-(3,5- di-tert-butyl-4-hydroxyphenylthio)succinimide, according to claim 1.

* * * * *